United States Patent [19]

Wong

[11] 4,293,537

[45] Oct. 6, 1981

[54] NOVEL CHEMICAL METHOD OF LABELING PROTEINS WITH $^{99m}$TC-TECHNETIUM AT PHYSIOLOGICAL CONDITION

[76] Inventor: Dennis W. Wong, 2853 Sunnyglen Rd., Torrance, Calif. 90505

[21] Appl. No.: 939,820

[22] Filed: Sep. 5, 1978

[51] Int. Cl.$^3$ .................... A61K 49/00; A61K 43/00; C07G 7/00
[52] U.S. Cl. .................................. 424/1; 260/112 B; 424/9; 424/1.5
[58] Field of Search ................................ 424/1, 9, 12; 260/112 B

[56] References Cited

U.S. PATENT DOCUMENTS

| | | | |
|---|---|---|---|
| 3,812,245 | 5/1974 | Dugan | 424/1 |
| 4,057,617 | 11/1977 | Abramovici et al. | 424/1 |
| 4,094,965 | 6/1978 | Layne et al. | 424/1 |

OTHER PUBLICATIONS

Wong et al., J. Nucl. Med. 20: 967, 1979.

Primary Examiner—Benjamin R. Padgett
Assistant Examiner—Christine M. Nucker

[57] ABSTRACT

A novel rapid chemical method of labeling exogenous and autologous plasma proteins, other compound and-/or substance containing proteins with $^{99m}$Tc-Technetium at physiologic pH 7.4 condition, producing a sterile apyrogenic radioactive tracer material which is suitable for biological and medical uses.

9 Claims, No Drawings

NOVEL CHEMICAL METHOD OF LABELING PROTEINS WITH $^{99m}$TC-TECHNETIUM AT PHYSIOLOGICAL CONDITION

BACKGROUND OF THE INVENTION

Pulmonary embolism is the commonest preventable cause of death in hospitalized patients. Early detection of its most common precursor, venous thrombosis of the lower extremities, would permit prompt anticoagulant therapy and reduce the frequency of embolism. However, the potential for successful treatment of established pulmonary embolism is limited by the short time between onset of symptoms and death in the majority of patients who die of massive pulmonary embolism. Secondly, most patients with massive pulmonary embolism do not have preceding clinical signs of minor venous thromboembolism, even though postmorten examination shows that most of them do have associated leg vein thrombosis. Unfortunately, clinical diagnosis of venous thrombosis and phlebographic technique are neither specific nor reliable during acute phase of thrombophlebitis. There is an urgent need for a simple, rapid and reliable means of detecting venous thrombosis. A number of techniques for screening large numbers of high-risk patients are being evaluated at present. The most promising appears to be radioiodinated fibrinogen labeled with $^{125}$I. Because of low energy gamma photon and long physical half life, the use of $^{125}$I-fibrinogen is limited to surface monitoring technique. It is not a scintillation imaging agent. Other limitations include high percentage of false positive results due to its inability to distinguish between superficial and deep vein thrombi, and its sensitivity to fibrin in hematoma and inflammatory exudate. Autologous human fibrinogen labeled with $^{131}$I has been advocated recently as a thrombi scanning agent.

Another important group of plasma protein which may have significant clinical applications in Nuclear Medicine is immunoglobulins or antibodies. The immunoglobulins are protein molecules that carry antibody activity against specific antigens. With the possible exception of natural antibody, antibodies arise in response to foreign substances such as microorganisms, toxin or other foreign matter introduced into the body. The immunoglobulins comprise a heterogeneous group of proteins, chiefly gamma or beta globulins, which account for approximately 20% of the total plasma proteins. The presence of malignant tumors can also cause the production of antibodies within the host in response to the insult. Thus, radiolabeled autologous immunoglobulin isolated from patient's own serum which contains the specific antibody offers the best and specific means of detecting infectious foci or tumors. Early detection of these leisons is extremely important in reducing the high morbidity and mortality rate. The use of $^{131}$I-labeled antigen or antibody for tumor imaging in man have been reported in the literature.

Various methods of labeling plasma proteins with $^{125}$I or $^{131}$I have been published in recent years. The most commonly used chemical method is radio-iodination of the protein in the presence of chloramine-T or iodine monochloride. The labeling yield, however, is low and varies from 50-70%. In order to be clinically useful, the desired radiolabeled protein must undergo a long and tedious separation and purification process. The radionuclide $^{131}$I has other disadvantages. Among these are: emission of high energy beta and gamma photons which is not compatible with existing commercial display means; a long physical half life of 8 days; excessive irradiation to the patients; and finally, the dosage of any $^{131}$I-labeled compounds must be given in very minute microcurie(uCi) quantity.

Compounds labeled with $^{99m}$Tc which eliminate most of the undesirable properties of the radioiodinated radiopharmaceuticals have been found extremely useful in biological studies and medical diagnosis. The radionuclide, $^{99m}$Tc-technetium, has many advantages. It is a pure gamma emitter with a relative short half life of 6 hours. The gamma photon of 140 KeV energy is compatible with existing conventional scintillation imaging equipments. $^{99m}$Tc-labeled radiopharmaceuticals can be safely administered to the patients with a much larger dose than radioiodinated compounds but produces a minimal amount of radiation health hazard. Human proteins such as serum albumin labeled with $^{99m}$Tc has been used clinically in placenta localization, cardiac scan and cisternography. More recently, there is increasing scientific and medical interest in $^{99m}$Tc-labeled human fibrinogen and antibody for the localization and detection of thrombi, infectious foci and tumors. Unfortunately, a more wide spread use of these radioactive tracer materials has been restricted because; (1) a simple and reliable chemical method of labeling protein with $^{99m}$Tc at physiological condition which preserves the physiobiological properties of the protein has not been developed; (2) current $^{99m}$Tc-labeling technology using acid reduction of the radionuclide in the presence of a reducing agent causes complete denaturation of the proteins; (3) the labeling yield is low with many radioactive impurities as well as free or unbound $^{99m}$Tc: (4) the possibility of hepatitis transmission and antigenic reactions.

Recent literature mention labeling serum albumin with $^{99m}$Tc by a chemical process in the presence of a reducing agent such as stannous chloride ($SnCl_2.2H_2O$) or stannous tartrate (see U.S. Pat. No. 3,725,295 to Eckelman et al and U.S. Pat. No. 4,042,676 to Molenski et al), but the results have never been very satisfactory. According to the labeling methodology, $^{99m}$Tc(+7) in the stable form of sodium pertechnetate($Na^{99m}TcO_4$) is first reduced to a chemically active +4 or +5 valence state with a reducing agent in 0.5-1 N HCl at a pH of less than 2. A diluted solution of the albumin is added to the reduced $^{99m}$Tc/$SnCl_2$ acidic mixture with subsequent binding of the radionuclide to the protein ligand. The final mixture is than readjusted to pH 6-7 with a suitable buffer. The labeling mechanism is not known. Since the optimal condition of preserving the physiobiological properties of the protein is at a very narrow pH range of 7-7.4, proteins labeled by the above described chemical method is completely denatured.

The enzymes streptokinase and urokinase which are proteins, have been labeled with $^{99m}$Tc using similar technique. (see U.S. Pat. No. 3,812,245 to Dugan and Dugan, MA, Kozzar, JJ, et al, J. Nucl. Med. 14 233, 1973) The labeling yields of these proteins are extremely low. Purification of these radioactive proteins requires a tedious process of removing large amount of free or unbound $^{99m}$Tc, insoluble tin particles in the form of $^{99m}$Tc-stannous hydroxide($^{99m}$Tc-Sn(OH)$_4$), and other protein degradation products. (see Duffy MJ and Duffy GJ, J. Nucl. Med. 18: 483, 1977 and Person, BRR and Kempe, V. J. Nucl. Med. 16: 474, 1975)

$^{99m}$Tc-streptokinase and $^{99m}$Tc-urokinase have claimed to be effective in localizing preformed clots of the deep veins. However, they are ineffective in documenting early stage of acute thrombophlebitis. Both enzymes are antigenic in man.

An alternate approach for labeling proteins by chemical means has been patented in 1978 but has never been reported in any scientific scientific literature (see U.S. Pat. No. 4,057,617 to Abramovici et al). According to this invention, the proteins antibody and fibrinogen are labeled with $^{99m}$Tc at pH 11.6. A careful analysis of the labeling methodology reveals many flaws. Stannous chloride dissolved in dilute hydrochloric acid(HCl) or acetic acid is known to be a powerful reducing agent for the reduction of $^{99m}$TcO$_4^-$. Increasing the pH from 2 to 11.6 will not cause further reduction of $^{99m}$Tc. On the contrary, during the process of pH adjustment, insoluble radioactive collodial particles, stannous hydroxide, will form when alkali such as 0.1 N NaOH is added to a solution containing SnCl$_2$ and reduced $^{99m}$Tc. The problems encountered by labeling proteins at alkaline pH condition is similar to the acidic chemical method, namely; protein denaturation, formation of insoluble stannous particles, protein degradation byproduct, free or unbound $^{99m}$Tc and low yield.

Significant protein denaturation occurs with earlier electrolytic method of labeling serum albumin and fibrinogen with $^{99m}$Tc using zirconium electrodes in acid medium (see U.S. Pat. No. 3,784,453 to Dworkin et al; Benjamin, PP, Int. J. Appl. Rad. Isotopes 20: 187, 1969; Dworkin, HJ and Gutkowski, RF, J. Nucl. Med. 12: 562, 1971 and Wong, DW and Mishkin, F, J. Nucl. Med. 16: 347, 1975). The labeling methodology requires the addition of the protein to be labeled to an acidic medium (pH 1.8) during electrolysis which leads to subsequent decomposition of the labeled product. Recently, an improved electrolytic method of labeling plasma proteins has been developed (see Wong, DW, J. Labeled Comp. Radiopharmaceuticals 14: 603, 1978 and Wong, DW and Huang, TT, Int. J. Appl. Rad. Isotopes 28:719, 1977). These proteins are labeled at physiological conditions, thus avoiding harsh treatment of the protein molecules and preserving the physiobiological properties. The labeling mechanism is not well understood. The tagging of $^{99m}$Tc to pure protein appears to involve a chemically active $^{99m}$Tc-(Zr)citrate complex species with high protein binding capacity. The latter is formed following initial reduction of $^{99m}$TcO$_4^-$ by Zr$^{++}$ ions as a result of electrolysis and by the addition of trisodium citrate/NaOH buffer during pH adjustment. In the presence of a pure protein, such as fibrinogen or immunoglobulin, $^{99m}$Tc quickly binds to the protein ligand. Whether the entire complex binds to the protein ligand or acts only as a transferring agent for reduced $^{99m}$Tc for the final labeling has not been determined. Further investigation of the improved electrolytic technique indicates that similar complex species can be prepared by chemical means with stannous chloride or stannous tartrate under similar conditions. The resultant $^{99m}$Tc-(Sn)citrate complex species is effective in tagging plasma proteins with superior labeling efficiency and reproducibility. The labeling mechanism of the chemical method has not been determined. It is assumed that protein binding involves the reaction of the $^{99m}$Tc-(Sn)-citrate complex species with the protein ligand similar to the $^{99m}$Tc-(Zr)-citrate reaction (see Wong, DW, Mishkin, F and Lee, T, Int. J. Appl. Rad. Isotopes 29: 251, 1978).

SUMMARY OF THE INVENTION

Human plasma proteins are labeled with $^{99m}$Tc-pertechnetate by a novel chemical process at physiologic pH 7.4. Autologous human fibrinogen and immune gamma globulin extracted by glycine precipitation and the salting-in action of rivanol respectively have been tagged by the same technique with similar high yields. The labeling methodology requires the initial reduction of $^{99m}$Tc-pertechnetate in normal saline by stannous chloride in 0.05 N HCl solution. Following pH adjustment to 7.4 with a solution of trisodium citrate and NaOH, a stable $^{99m}$Tc-(Sn)citrate complex species with high protein binding capacity is formed. In the presence of pure protein, the radionuclide $^{99m}$Tc quickly binds to the protein ligand at ambient temperature. Greater than 95% of the initial radioactivity is found to be associated with the labeled protein; 3-4% unbound $^{99m}$Tc(Sn) complex and less than 1% free or unbound $^{99m}$TcO$_4^-$ as assessed by paper radiochromatography and instant thin layer radiochromatography. Since these proteins are labeled at optimal physiological condition, the problems of protein denaturation normally associated with earlier labeling technology have been significantly reduced. In vitro experimental data indicate no significant loss of physiobiological properties. The entire labeling process which requires less than 1 hour of time produces a sterile pyrogen-free solution of $^{99m}$Tc labeled tracer material ready for patient administration. No further purification of the final labeled product is necessary. This novel labeling technique will provide a simple mean of tagging autologous fibrinogen or antibodies with $^{99m}$Tc for scintillation imaging which may allow visualization of thrombi, infectious lesions or tumors by scanning techniques.

DETAILED DESCRIPTION OF THE INVENTION

The labeling methodology in the present invention requires (1) initial reduction of $^{99m}$Tc-pertechnetate to a chemically active +4 or +5 valence state by a reducing agent such as stannous chloride; (2) the formation of a stable chemically active $^{99m}$Tc-(Sn)citrate complex species and (3) the covalent binding of radionuclide to the protein ligand. Chemical reduction of $^{99m}$Tc-pertechnetate can be effectively carried out with any suitable reducing agents such as SnCl$_2$, SnF or stannous tartrate. However, stannous chloride (SnCl$_2$.2H$_2$O) is preferred in the present embodiment. The stannous chloride reagent is freshly prepared by dissolving the desired amount of SnCl$_2$.2H$_2$O powder or crystals in 6 N HCl and diluted with distilled water to a final concentration of 0.2 mg SnCl$_2$/ml 0.05 N Hcl slution. After dissolving, the stannous chloride solution is sterilized by passage through a 0.22 nm biological filter and injected into individual sterile and non-pyrogenic serum vials. Each vial contains 0.5 ml of the sterilized reducing agent which can be stored under refrigeration at 2°-8° C. until needed. These vials are preferably lyophilized by conventional freeze-drying techniques to remove water. This provides a solid mixture of stannous chloride and 0.05 N HCl which aids in shipping and storage and is more stable than in liquid reagent form. The lyophilized reducing agent can be reconstituted by the addition of 2-3 ml $^{99m}$Tc-pertechnetate in normal saline without losing its reducing activity. The concentration of the reducing agent can be varied from 0.2-5 mg/ml depending upon the amount of $^{99m}$Tc radioactivity used in the labeling process. The concentration of 0.1 mg $SnCl_2$ in 0.5 ml 0.05 N HCl is sufficient to reduce 60-100 mCi of $^{99m}TcO_4^-$.

In the preferred embodiment, 2-3 ml of $^{99m}$Tc-pertechnetate in normal saline which provides 60-100 mCi of $^{99m}$Tc radioactivity is aseptically injected into the reaction vial containing the stannous chloride reducing agent in either liquid or lyophilized form. The radioactive content of the reaction vial is then shaken for 1-10 minutes to allow complete reduction of $^{99m}$Tc-pertechnetate. The source of $^{99m}$Tc-technetium is preferably obtained in the form of fresh sodium pertechnetate in normal saline eluted from a $^{99m}$Tc generator.

In accordance with the principles of this invention, a sufficient amount of 2% trisodium citrate solution previously adjusted to pH 12.4-12.6 with 1 N NaOH is used to react with the reduced $^{99m}$Tc ions. The addition of this reagent not only cause the formation of the radioactive complex species but also raise the acidic $^{99m}$Tc-$SnCl_2$-HCl mixture from pH 1.8 to 7.4. Experimental data indicate that the reduced $^{99m}$Tc ion in the form of $^{99m}$Tc-(Sn)citrate complex is stable and chemically active at a pH range of 5-9 indefinitely in the absence of air or any oxidizing agents. However, to preserve the physiobiological properties of the protein and to obtain high labeling yield, a pH 7.4 condition is preferred. Any of the commonly used alkaline buffer systems with a pH of greater than 7 can be utilized to form the radioactive complex species with $^{99m}$Tc. Among these are sodium acetate, sodim bicarbonate or sodium phosphate. Sodium citrate is preferred in the present formulation because it is physiobiochemically compatible with many biological preparations and because sodium citrate is an excellent biological preservative.

While it is preferred that a solution of trisodium citrate/NaOH with a pH of 12.4 is used to produce the radioactive complex species and to raise the pH to 7.4 condition as an one-step process, this chemical reaction can be separated into two successive steps. The radioactive $^{99m}$Tc-(Sn)citrate complex species can be formed by the addition of 1 ml of a 2% solution of trisodium citrate(pH 8.5) to the reduced $^{99m}$Tc-$SnCl_2$-HCL mixture prior to pH adjustment. After thorough mixing, the pH of the admixture is then raised to 7.4 with 0.1-1 N NaOH solution. The amount of NaOH solution needed can be determined by routine experimentation to those skilled in the art.

Following pH adjustment and the formation of the radioactive complex, a diluted solution of the protein to be labeled is added to the mixture. The radionuclide is quickly bound to the protein ligand and is stablized at 37° C. or at room temperature for 30 minutes. The amount of protein that can be labeled varies from 0.1-100 mg. In the present invention, a concentration of 3-4 mg of protein in 1 ml diluent is adequate to bind up to 100 mCi of $^{99m}$Tc. Diluents such as distilled water, normal saline or any pharmacologically acceptable buffer systems such as Sorenson's phosphate buffer or Veronal buffer can be used to reconstitute or to dilute the protein to the desired concentration.

Exogenous protein preparations are commercially available in sterile apyrogenic solutions or in lyophilized forms. In order to demonstrate the efficacy of the present labeling technique for tagging plasma proteins, the following representative agents are used;
(A) Plasma proteins:
Human fibrinogen, 20 mg/ml
Human serum albumin, salt poor, 25%
Human immune gamma globulin, 16%
(B) Enzyme:
Thrombin, bovine, 1000 units/ml normal saline
(C) Hormone:
Thyrotropin, bovine, 10-50 units/ml normal saline
(D) Autologous plasma proteins:
Human fibrinogen
Canine fibrinogen
Human immune gamma globulin All exogenous protein preparations are prepared according to manufacturer's direction. The amount of protein to be labeled is limited to 1-20 mg in less than 1 ml diluent.

Autologous human or canine fibrinogen and human immune γ-globulin are obtained from plasma or serum by the modified methods of Kazai (Kazai LA, Amesl S, Miller OP et al, Proc Soc. Exptl. Biol. Med. 113: 989, 1963) and Horejsi and Smetana (Horejsi, J and Smetana, R, Acta Medica Scand. 155: 65, 1956) respectively. Qualitative analysis of the extracted proteins using protein electrophoresis demonstrate absence of any contaminants. The extracted autologous proteins are dissolved in Sorenson phosphate pH 7.4 buffer to a final concentration of 3-4 mg/ml. No significant loss of biological property occurs following extraction procedure as indicated by biochemical determinations.

The binding efficiency of the labeled proteins is assessed by ascending paper and instant thin layer radiochromatography with silica gel plates in 85% methanol. The actual amount of labeled protein content is determined by trichloroacetic acid(TCAA) protein precipitation method. In case of $^{99m}$Tc-labeled fibrinogen, topical thrombin solution is added prior to TCAA protein precipitation in order to determine the actual amount of clottable protein present after labeling. Qualitative radiolabeled protein identification is determined by protein electrophoresis using cellulose polyacetate support medium.

Results from analysis of a series of at least 12 trials for each labeled protein indicate that an average binding efficiency of greater than 95% (range 95-99%) is achieved as assessed by radiochromatography with less than 1% free or unbound $^{99m}TcO_4^-$. TCAA protein precipitation determinations demonstrate the existance of a reduced unbound species, presumably, $^{99m}$Tc(Sn) complex which accounts for 3-4% of the radioactivity. Electrophoris protein profiles are identical for both labeled or unlabeled protein fractions. Greater than 95% of the radioactivity is firmly bound to the protein. Thrombin clottability assays indicate that $^{99m}$Tc-fibrinogen retains most of its biological activity after labeling. The final labeled fibrinogen contains greater than 85% clottable protein with an average clottability of 95%. Similary, the labeling process does not affect the enzymatic property of $^{99m}$Tc-thrombin. All $^{99m}$Tc-labeled proteins are stable at room temperature up to 6 hours after tagging process as determined by radiochromatography and protein electrophoresis. The final labeled product is sterile, apyrogenic up to seven days without any evidence of microorganism contamination.

Since proteins are essential constituents in animal and plant, a physiological chemical method of labeling these substances with a radioactive tracer offers unlimited potential in biological investigations and medical uses. $^{99m}$Tc-labeled autologous human fibrinogen, for example, is extremely useful for the localization and detection of thrombi or emboli in man by scintillation imaging techniques. Similarly, infectious foci or tumors can be specifically detected using $^{99m}$Tc-labeled autologous immunoglobulins. A dose of 3–20 mCi in 1–3 ml volume of the radiolabeled autologous proteins administered intravenously to patients is sufficient to detect these lesions. Whole body scans are then taken at various time intervals, e.g. 0.5–24 hrs post administration of the dose using a rectilinear scanner or Anger scintillation camera. Increased radioactivity at the site of the lesions indicates the presence of thrombi, emboli, infectious foci or tumors.

The present invention is far superior to earlier reported labeling techniques. All components used in the composition are prepared in bulk quantity and sterilized by passage through a 0.22 nm biological filter into sterile, apyrogenic serum vials. An instant "cold" labeling kit comprising a stannous reducing agent and an alkaline trisodium citrate/NaOH reagent can be prepared in advance prior to labeling of the protein with $^{99m}$Tc-pertechnetate. The following examples illustrate the simiplicity and usefulness of the present invention for labeling different types of plasma proteins.

EXAMPLE 1

Labeling procedure for $^{99m}$Tc-exogenous or autologous fibrinogen

1. Inject up to 2 ml (60–100 mCi) $^{99m}$Tc-pertechnetate in normal saline into a sterile evacuated serum vial containing 0.5 ml of a solution of 0.1 mg $SnCl_2$ in 0.05 N HCl solution. Mix the content of the vial vigorously for one minute and allow to stand at room temperature for a total of 10 min. for the complete reduction of $^{99m}TcO_4^-$.
2. Raise the pH of the mixture to 7.4 by adding 0.5–0.75 ml 2% (0.068 M) trisodium citrate solution previously adjusted to pH 12.4–12.6 with 1 N NaOH.
3. Immediately, inject 0.2 ml (4 mg) reconstituted exogenous fibrinogen solution or 1 ml (3–4 mg) of autologous human fibrinogen dissolved in pH 7.4 (0.007 M) Sorenson's phosphate buffer into the vial slowly with gentle swirling to avoid foaming.
4. Incubate the content of the vial at room temperature for 30 min. The final labeled product is clear, sterile and ready for use. Additional purification process of the labeled protein is unnecessary.
5. Perform complete qualitative and quantitative radioactive assays. The final concentration should be in the range of 15–25 mCi labeled protein per ml.
6. For scintillation imaging, a dose of 3–15 mCi $^{99m}$Tc-autologous fibrinogen is sufficient to detect presence of blood clots in pulmonary embolism or thrombophlebitis.

EXAMPLE 2

Procedure for labeling $^{99m}$Tc-Human serum albumin

1. Following labeling procedure steps 1 & 2 of example 1, inject 0.1 ml (25 mg) normal serum albumin (25%, salt poor) into the vial slowly with gentle swirling to avoid foaming.
2. Complete steps 4 & 5 of example 1. A dose of 3–15 mCi is sufficient for placenta localization, cardiac scan or cisternography.

EXAMPLE 3

$^{99m}$Tc-Exogenous or autologous human immune gamma globulin(Antibody)

1. Following steps 1 & 2 of example 1, inject 0.1 ml(16.5mg) of exogenous human immune gamma globulin or 1 ml(1–20 mg) of autologous human gamma globulin(antibody) dissolved in pH 7.4 phosphate buffer into the vial slowly with gentle swirling. Complete steps 4 & 5 of example 1.
2. A dose of 3–15 mCi of the immunoglobulin is sufficient for the localization and detection of tumors or infectious foci.

EXAMPLE 4

Procedure for labeling enzyme with $^{99m}$Tc-pertechnetate

1. Dissolve lyophilized thrombin(bovine) in 5 ml normal saline or pH 7.4 phosphate buffer to a final concentration of 1000 units/ml.
2. Label 10–1000 units of the enzyme with 60–100 mCi $^{99m}$Tc-pertechnetate according to the labeling procedure described in example 1.

EXAMPLE 5

Procedure for labeling hormone with $^{99m}$Tc-pertechnetate

1. Dissolve 10 or more units of the hormone thyrotropin in 1 ml normal saline or pH 7.4 phosphate buffer.
2. Labeled the desired amount of the hormone according to example 1.

The above examples and detailed described procedures are for illustration purposes only and are not intended to be limiting of the scope of the invention. It will be apparent to those skilled in the art that both may be modified within the scope of the invention defined in the following claims:

I claim:

1. A method of labeling human or animal plasma proteins, compounds or substances containing proteins with $^{99m}$Tc-pertechnetate at physiological pH 6–8 condition comprising the sequential steps of:
   a. treating 2–3 ml(60–100 mCi) $^{99m}$Tc-pertechnetate in normal saline with 0.5 ml of a solution of 0.1–5 mg stannous chloride or stannous tartrate in 0.05 N hydrochloric acid solution at room temperature for about 10 minutes;
   b. raising the pH of the acidic mixture of step (a) to 7.4 with a sufficient amount of pH 12.4 trisodium citrate/NaOH solution;
   c. adding from 0.1–50 mg of the desired protein to be labeled in less than 1 ml diluent to the admixture of step (b) and incubating at 37° C. or at room temperature for 30 minutes.

2. A method of detecting thromboembolism in patients by intravenous administration of 3–15 mCi $^{99m}$Tc-autologous human fibrinogen labeled according to the method of claim 1 and observing areas of increased radioactivity at the site of blood clots or active thrombosis as seen in scintigraphic scans.

3. Human serum albumin is labeled with $^{99m}$Tc according to the method of claim 1.

4. Human fibrinogen is labeled with $^{99m}$Tc according to the method of claim 1.

5. Human immunoglobulin is labeled with $^{99m}$Tc according to the method of claim 1.

6. A protein enzyme thrombin(bovine) is labeled with $^{99m}$Tc according to the method of claim 1.

7. A protein hormone thyrotropin(bovine) is labeled with $^{99m}$Tc according to the method of claim 1.

8. A method of detecting infectious foci in patients by intravenous administration of 3-15 mCi $^{99m}$Tc-autologous human immunoglobulin labeled according to the method of claim 1 which contains the specific antibody against the antigen or microorganisms and observing areas of increased radioactivity at the sites of the infection as seen in scintigraphic scans.

9. A method of detecting benign or malignant tumors in patients by intravenous administration of 3-15 mCi $^{99m}$Tc-autologous human immunoglobulin labeled according to the method of claim 1 which contains the specific antibody against the specific tumor and observing areas of increased radioactivity at the sites of tumors or metastasis as seen in scintigraphic scans.

* * * * *